(12) United States Patent
Balcke et al.

(10) Patent No.: US 8,586,367 B2
(45) Date of Patent: Nov. 19, 2013

(54) METHODS FOR ANALYZING POLAR METABOLITES OF THE ENERGY METABOLISM

(75) Inventors: Gerd Balcke, Potsdam (DE); Tilmann B. Walk, Kleinmachnow (DE); Martin Dostler, Henningsdorf (DE); Ralf Looser, Berlin (DE); Susan Carvalho, Berlin (DE)

(73) Assignee: BASF Plant Science Company GmbH (DE)

( * ) Notice: Subject to any disclaimer, the term of this patent is extended or adjusted under 35 U.S.C. 154(b) by 42 days.

(21) Appl. No.: 13/382,250

(22) PCT Filed: Jul. 7, 2010

(86) PCT No.: PCT/EP2010/059740
§ 371 (c)(1),
(2), (4) Date: Jan. 4, 2012

(87) PCT Pub. No.: WO2011/003945
PCT Pub. Date: Jan. 13, 2011

(65) Prior Publication Data
US 2012/0107940 A1    May 3, 2012

Related U.S. Application Data

(60) Provisional application No. 61/228,165, filed on Jul. 24, 2009.

(30) Foreign Application Priority Data

Jul. 8, 2009 (EP) .................................... 09164949

(51) Int. Cl.
*G01N 33/48* (2006.01)
*G01N 1/18* (2006.01)
*C12Q 1/02* (2006.01)

(52) U.S. Cl.
USPC .............. 436/63; 436/111; 436/124; 436/161; 436/173; 436/174; 436/175; 436/177; 436/178; 435/29; 435/325

(58) Field of Classification Search
USPC ........... 436/63, 106, 111, 124, 161, 173, 174, 436/175, 177, 178; 422/68.1, 69, 70, 72, 422/89, 527, 533; 435/4, 29, 325
See application file for complete search history.

(56) References Cited

U.S. PATENT DOCUMENTS

| | | | |
|---|---|---|---|
| 4,540,884 A | 9/1985 | Stafford et al. | |
| 5,397,894 A | 3/1995 | Wells et al. | |
| 7,311,838 B2 * | 12/2007 | Herold et al. | 210/639 |
| 7,431,841 B2 * | 10/2008 | Herold et al. | 210/634 |
| 2002/0151579 A1 | 10/2002 | Kasitu et al. | |
| 2004/0259221 A1 | 12/2004 | Zhao | |
| 2005/0037386 A1 | 2/2005 | Morrison et al. | |

OTHER PUBLICATIONS

Andersen et al. Journal of Agricultural Food Chemistry, vol. 54, 2006, pp. 4517-4523.*
Niessen, W.M.A, et al., "Liquid Chromatography-Mass Spectrometry General Principles and Instrumentation", Journal of Chromatography A, 1995, vol. 703, pp. 37-57.
Villas-Bôas, S.G., et al., "Cold Glycerol-Saline: The Promising Quenching Solution for Accurate Intracellular Metabolite Analysis of Microbial Cells", Analytical Biochemistry, vol. 370, (2007), pp. 87-97.
Sellick, C.A., et al., "Effective Quenching Processes for Physiologically Valid Metabolite Profiling of Suspension Cultured Mammalian Cells", Analytical Chemistry, vol. 81, No. 1, (2009), pp. 174-183.
Biondi, P.A., et al., "Gas Chromatographic Determination of Urinary 3-Methoxy-4-Hydroxyphenylethyleneglycol Sulphate After its Ion-Pair Extraction", Clinica Chimica Acta, vol. 121, (1982), pp. 79-86.
Faijes, M., et al., "Comparison of Quenching and Extraction Methodologies for Metabolome Analysis of *Lactobacillus plantarum*", Microbial Cell Factories, vol. 6, No. 27, (2007), pp. 1-8.
Imawari, M., et al., "A Simple and Sensitive Assay for 25-Hydroxyvitamin D, 24,25-Dihydroxyvitamin D and 1,25-Dihydroxyvitamin D in Human Serum", Clinica Chimica Acta, vol. 124, (1982), pp. 63-73.

* cited by examiner

*Primary Examiner* — Maureen Wallenhorst
(74) *Attorney, Agent, or Firm* — Novak Druce Connolly Bove + Quigg LLP

(57) ABSTRACT

The present invention is concerned with the analysis of polar metabolites and provides methods for analyzing polar metabolites including extracting a biological sample with a extraction buffer containing a phase separator and a volatile neutral ammonium salt under conditions which allow for immediate disruption of cells in the biological sample, separating the polar metabolites in the extract by chromatography, and analyzing the separated polar metabolites. Moreover, a method for quenching a biological sample containing cellular material is contemplated.

15 Claims, 8 Drawing Sheets

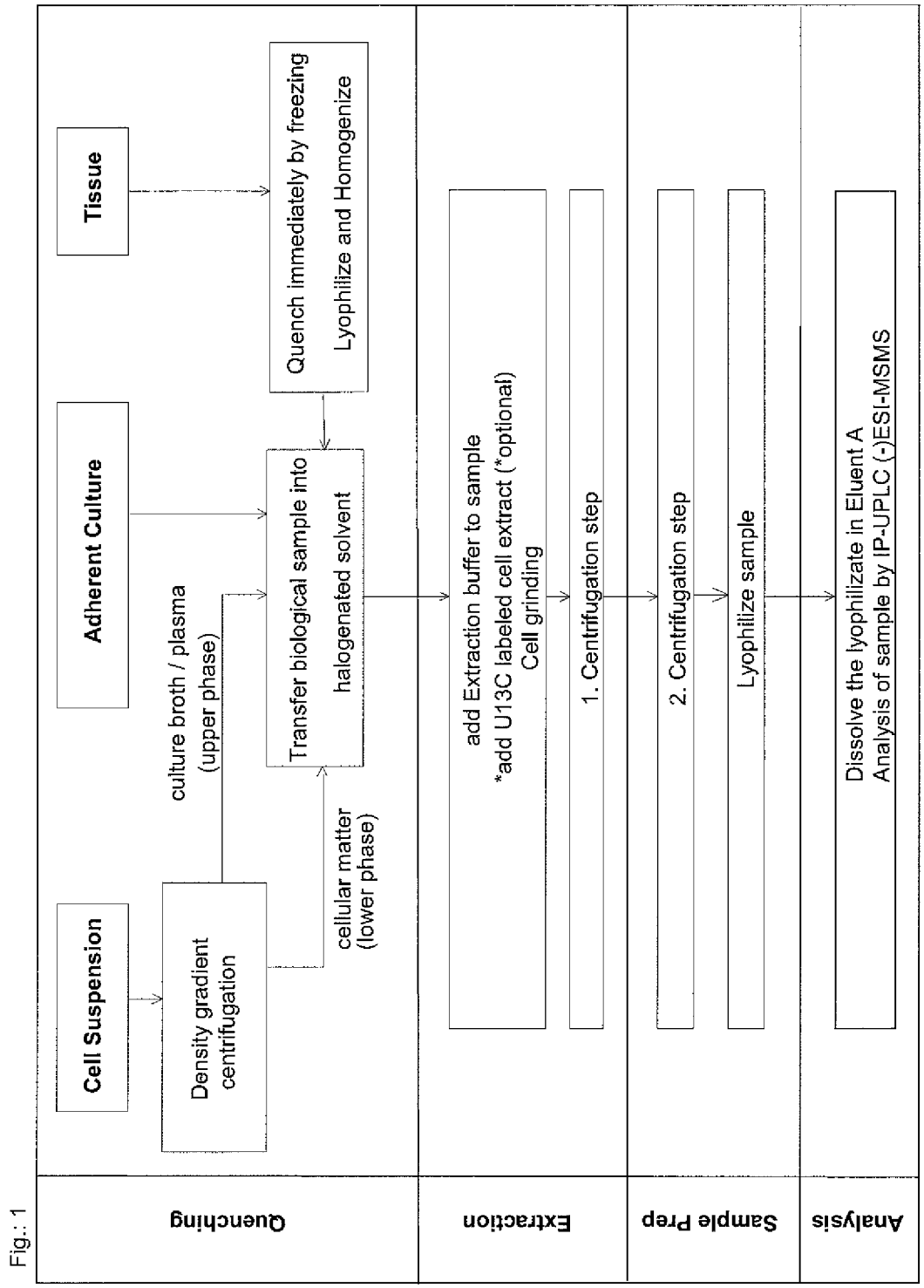

Fig.: 2
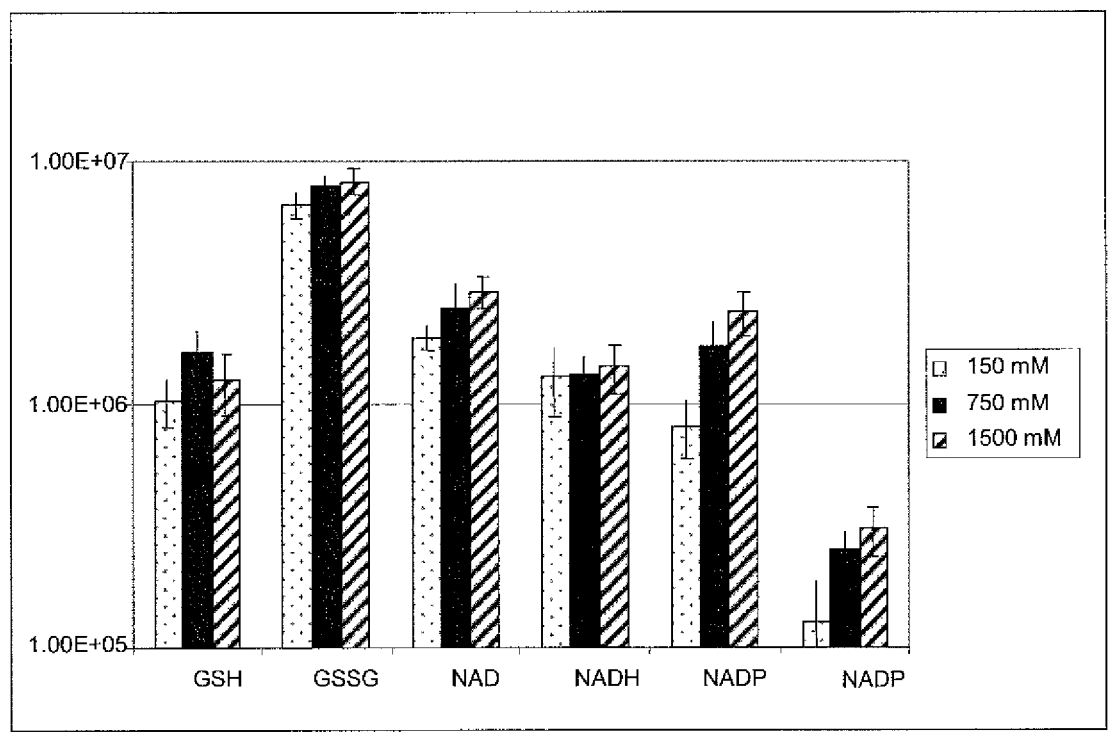

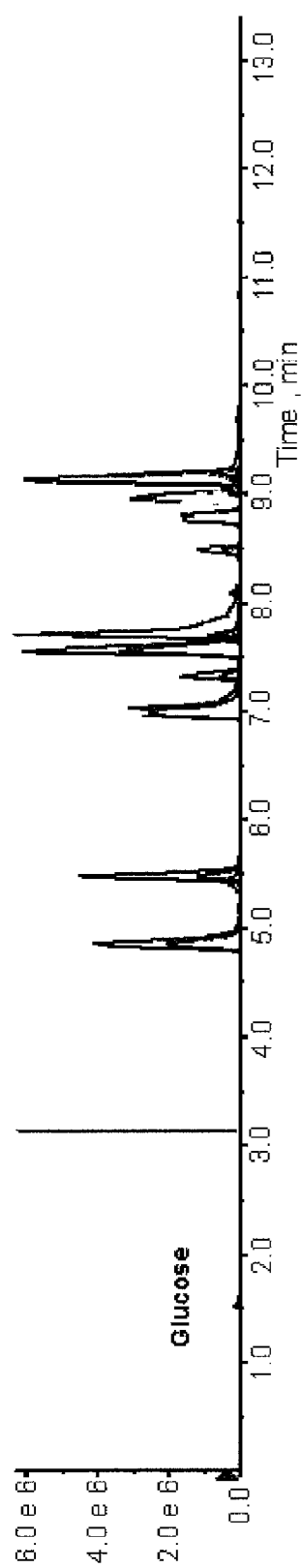
Fig.: 3A

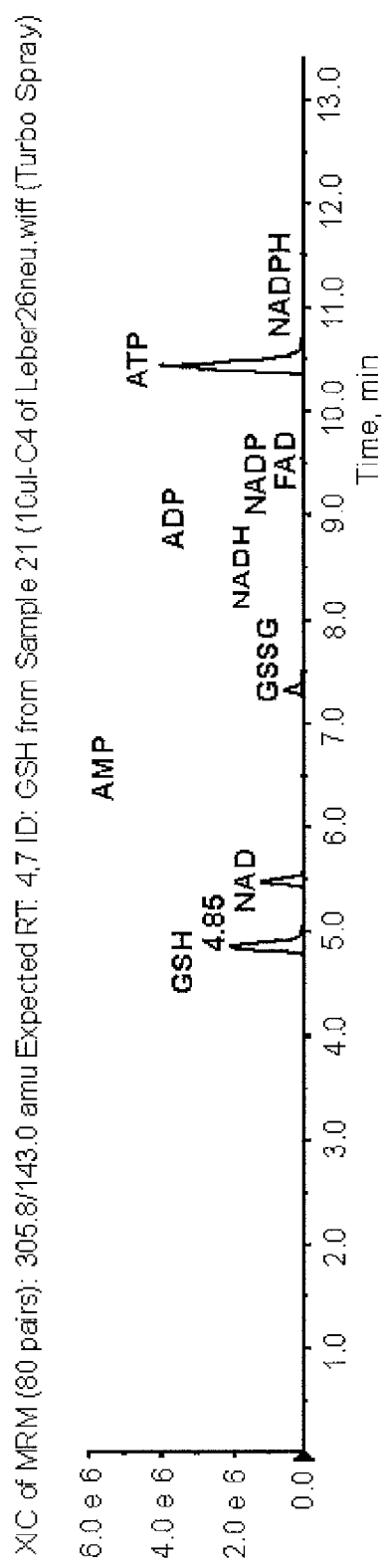
Fig.: 3B

Fig.: 3C
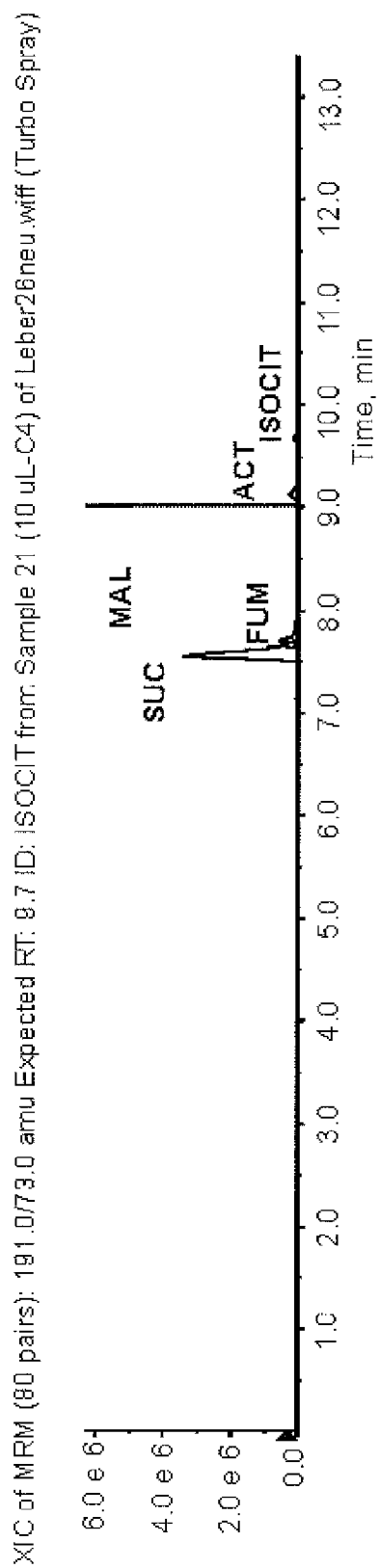

Fig.: 3D
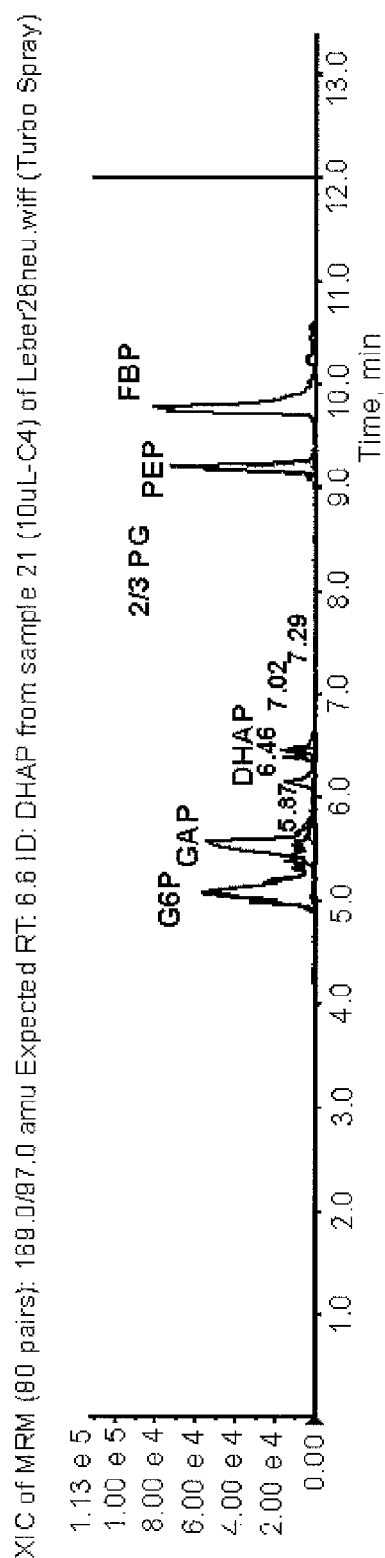

Fig.: 4A
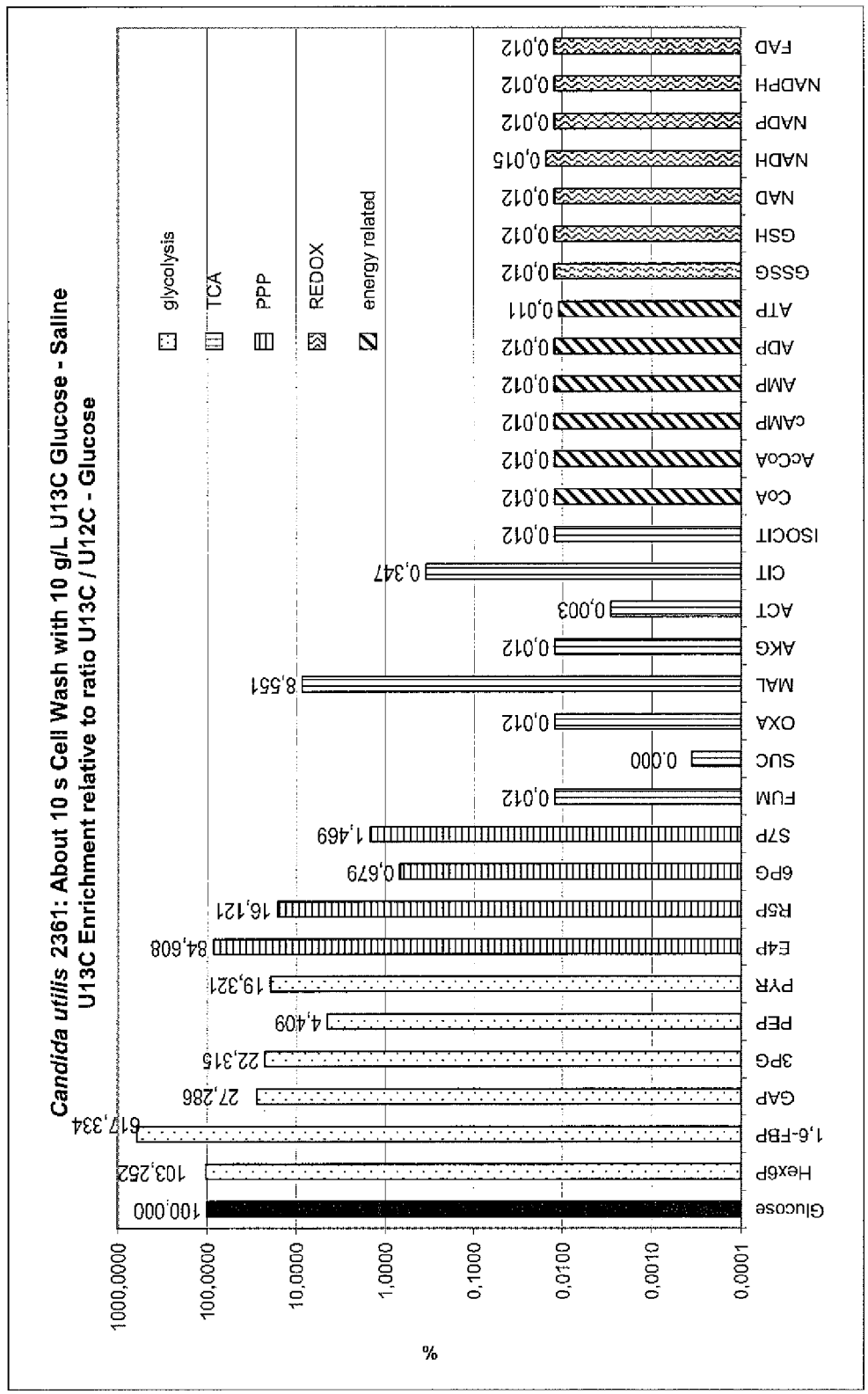

Fig.: 4B
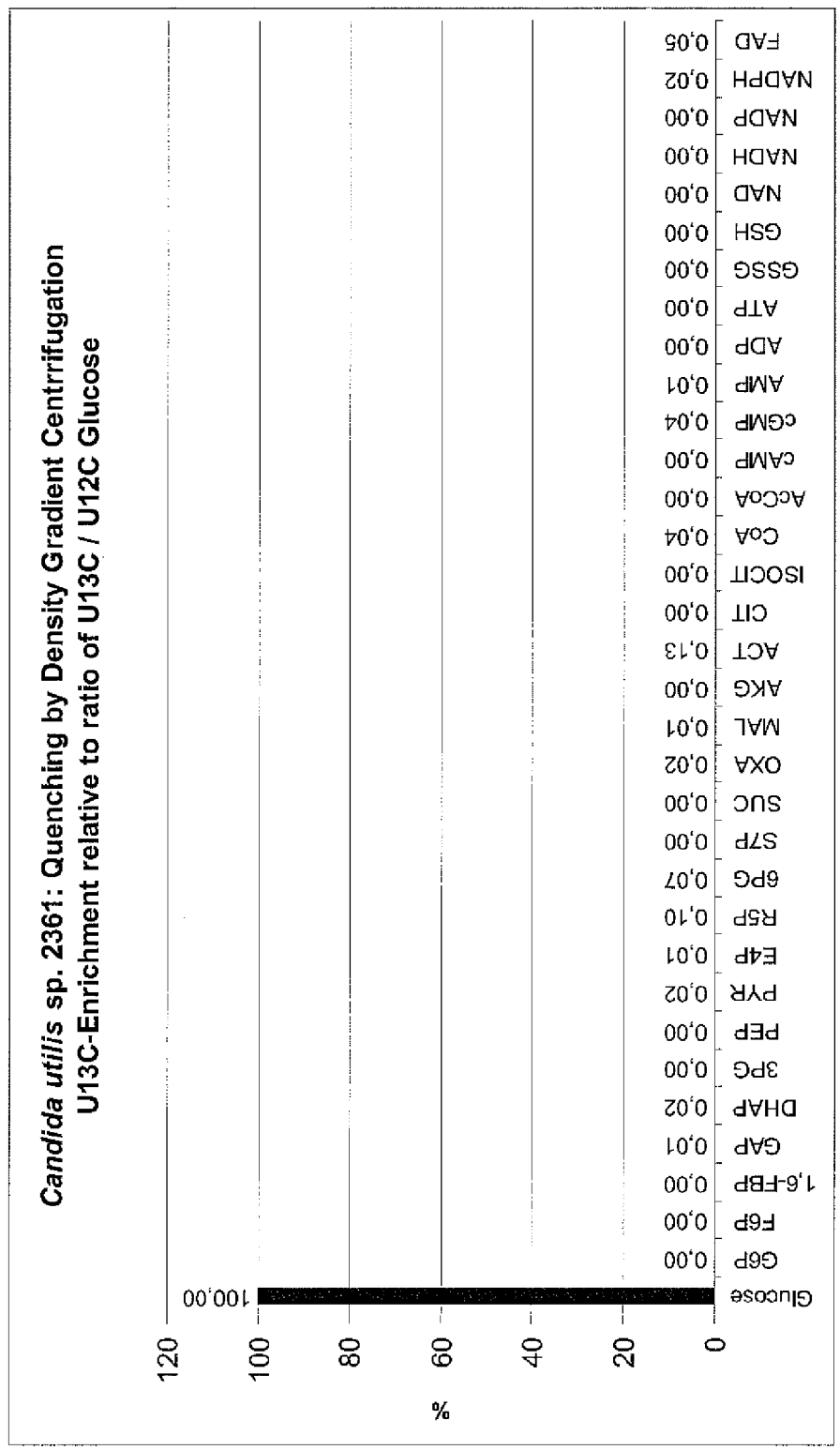

METHODS FOR ANALYZING POLAR METABOLITES OF THE ENERGY METABOLISM

RELATED APPLICATIONS

This application is a national stage application (under 35 U.S.C. §371) of PCT/EP2010/059740, filed Jul. 7, 2010 which claims benefit of European Application No. 09164949.1 filed Jul. 8, 2009 and U.S. Provisional Application No. 61/228,165, filed Jul. 24, 2009.

The present invention is concerned with the analysis of polar metabolites and provides methods for analyzing polar metabolites comprising extracting a biological sample with an extraction buffer comprising a phase separator and a volatile neutral ammonium salt under conditions which allow for immediate disruption of cells comprised by the biological sample, separating the polar metabolites comprised by the extract by chromatography, and analyzing the separated polar metabolites. Moreover, a method for quenching a biological sample comprising cellular material is contemplated.

Polar metabolites such as carboxylated or phosphorylated metabolites account for up to 90% of the metabolome of a cell. Accordingly, metabolomics, i.e., the systematic and comparative analysis of the metabolomes, to a significant extent concerns the analysis of polar metabolites.

The currently available analysis technology for metabolomics is essentially based on either liquid or gas chromatography-based mass spectrometry or liquid or gas chromatography-based NMR spectroscopy.

The drawback of the application of gas chromatography in metabolomics is that the metabolites must be transferred into the gaseous phase without destruction of the molecule. Derivatization is used to improve said conversion. However, derivatization also has some drawbacks since derivatization artefacts can occur which can be sometimes hardly distinguished from real metabolites.

Liquid chromatography does neither require the conversion into gaseous phase nor derivatizations. However, it is less effective regarding the separation of polar metabolites. Moreover, due to the presence of proteins, peptides and inorganic salts in biological samples in an excessive amount, the separation capacity for polar metabolites is normally drastically reduced.

Accordingly, it would be desirable to combine the precise separation characteristic of gas chromatography with the gentle conditions which can be applied for liquid chromatography. However, the aforementioned drawbacks shall be avoided.

Thus, methods for an efficient extraction and analysis of metabolites are not yet available but nevertheless highly desired.

The present invention relates to a method for analyzing polar metabolites comprising:
i) extracting a biological sample with an extraction buffer comprising a phase separator and a volatile neutral ammonium salt under conditions which allow for immediate disruption of cells comprised by the biological sample,
ii) separating the polar metabolites comprised by the extract obtained in step i) by chromatography, and
iii) analyzing the separated polar metabolites obtained in step ii).

The term "biological sample" as used herein refers to samples comprising biological material from all biological sources. It will be understood that the biological material shall comprise metabolites. Preferred material comprised by biological samples is cellular material such as cells or cellular fractions. Thus, preferably, the biological sample comprises suspension cells, adherent cells or tissues or fractions of any of these. Preferred biological samples comprise biological material from clinical sample including samples of body fluids, preferably, blood, plasma, serum, lymph, sudor, saliva, tears, sperm, vaginal fluid, faeces, urine or cerebrospinal fluid, or samples derived, e.g., by biopsy, from cells, tissues or organs. Also preferably, the biological sample represents one of various conditions of an organism, e.g., it can be derived from a healthy or diseased organism, an organism treated with a drug or an untreated organism etc. Also encompassed are biological samples comprising microorganisms such as bacteria or fungi or plants, plant parts (such as leaves, stems, roots, or flowers) or plant seeds.

The term "metabolites" as used herein refers to small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health as well as for plant growth. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da. Among the metabolites, the present invention envisages the polar metabolites, i.e. small molecule compounds being polar.

Extraction of molecules such as polar metabolites from a biological sample is a well known procedure which is based on using differences in the solubility of molecules. Molecules of interest may be extracted, i.e. dissolved, in an extraction buffer and, thus, be removed from a biological source. It will be understood that based on the chemical properties of the extraction buffer, different kinds of molecules can be dissolved and, thus, separated from the biological sample material. The method of the present invention, in particular, envisages the extraction of polar metabolites from biological samples. Extraction may be performed as continuous process or batch-wise. The extraction process in the case of biological samples is, preferably, supported by mechanically disrupting the biological material comprised by the biological sample. Such a support, preferably, allows for short and efficient extraction times of preferably less than 40 seconds, less than 30 seconds, less than 20 seconds. This can be achieved by well known homogenizing techniques such as cell grinding by for example pestilling or bead milling, e.g. FastPrep (MP Biomedicals, Germany).

The extraction buffer to be applied in the method of the present invention comprises a phase separator, i.e. a compound which is capable of facilitating and/or improving the separation of molecules into different phases such as phases of polar and non-polar molecules.

Preferably, the phase separator used in accordance with the method of the present invention comprises a halogenated solvent. Preferably, the halogenated solvent has a density larger than 1.01 g/cm$^3$ (at 20° C.). More preferably, the halogenated solvent is selected from the group consisting of dichloromethane, chloroform, or perchlorethylene, most preferably, it is dichlormethane. Phase separators which are highly hydrophobic and, preferably, denser than water, such as dichloromethane are preferred in the method of the present invention. These phase separators are capable of precipitating the proteins in a sample and, therefore, facilitate the preferably, centrifugation-based, removal of protein contaminants which otherwise would interfere with the subsequent analysis of the metabolites. Moreover, the phase separation by the phase separator is advantageous since the solubility of organic solvents in aqueous solutions will be reduced due to the high salt contaminations.

In addition to the halogenated solvent, the phase separator, preferably, comprises an alcohol of a lower alkane. Preferably, the said alcohol is ethanol, methanol or isopropanol and, most preferably, ethanol.

The halogenated solvent and the alcohol of a lower alkane are present in the phase separator, preferably, in a ratio of from 3:1 to 1:1, and preferably, in a ratio of 2:1. However, also preferably, the phase separator may also essentially consist of the halogenated solvent.

The extraction buffer, furthermore, comprises a volatile neutral ammonium salt. Volatile neutral ammonium salts as referred to herein are ammonium salts which can be sublimated by lyophilization procedures. Preferably, said volatile neutral ammonium salt is ammonium acetate, ammonium formiate, or ammonium hydrogencarbonate. Most preferably, the neutral ammonium salt is ammonium acetate. Specifically, ammonium acetate facilitates the separation of polar and non-polar metabolites since only the polar metabolites can be dissolved in an ammonium acetate containing extraction buffer according to the invention. Dependent on the kind of analysis to be performed for analyzing the metabolites, it might be necessary or helpful to separate the polar from the non-polar metabolites. This applies, in particular, if protein-containing samples are to be analyzed. Preferably, the extraction buffer comprises the said volatile neutral ammonium salt in a concentration of at least 0.5M. More preferably, a concentration of between 0.75M and 1.8M, and most preferably, a concentration of 1.5M is envisaged. It will be understood that the concentrations may include minor deviations, preferably in the range of plus or minus 15%, 10% or 5%. The use of an neutral (i.e. non-basic) volatile ammonium salt in the method of the present invention is advantageous over a basic volatile ammonium salt such as ammonium carbonate since such basic salts may alter the metabolic composition of a sample, e.g., by cleaving phosphorylated metabolites such as CoA-esters. The volatile neutral ammonium salt to be used in the method of the present invention, preferably, acts as a competitor for complexes comprising ionic metabolites and proteins. The particular high concentration of the neutral ammonium salt allows for a dissociation of said ionic metabolite-protein complexes due to the ion exchange properties of the said ammonium salt and, thus, increases the yield in ionic, i.e. polar, metabolites.

The extraction buffer, preferably, comprises other components as well such as solvents, stabilizers or, depending on further applications of the extract, standards for measurements. Preferred standards to be used in the extraction buffer are disclosed elsewhere in this specification in more detail.

It will be understood that the present invention also contemplates an extraction buffer as specified above.

The extraction of a biological sample in step i) can, in principle carried out at any temperature below the boiling point of the extraction buffer. Preferably, a temperature of less than 95° C. is envisaged and more preferably, the extraction is carried out at cold temperatures of less than −20° C. in order to avoid or reduce enzymatic activity or in order to reduce chemical reactions which chemically alter (e.g., degrade) the metabolites in the sample. Preferably, extraction is carried out at an extraction temperature between −20 to −80° C. Particular preferred temperatures are within the range of −25 to −80° C., −30° C. to −80° C., −35° C. to −80° C., −40° C. to −80° C., −45° C. to −80° C., −50° C. to −80° C., −55° C. to −80° C., −60° C. to −80° C., −65° C. to −80° C., −70° C. to −80° C. and, more preferably, the temperature is −70° C., −71° C., −71° C., −73° C., −74° C., −75° C., −76° C., −77° C., −78° C., −79° C., or −80° C.

The extracted polar metabolites are separated in the method of the present invention by conventional chromatographic techniques. Preferred techniques include capillary electrophoresis (CE), cation, anion exchange chromatography, size exclusion chromatography, reversed phase chromatography, normal phase chromatography, hydrophilic liquid interaction chromatography, immuno-affinity chromatography, liquid (LC) or gas chromatography (GC) as well as high pressure (HPLC) or ultra high pressure liquid chromatography (HPLC). Most preferably, separation is effected by HPLC or HPLC. For HPLC applications, C18 particles of <2.0 μm size are to be, preferably, used at a working pressure of from approx. 400 to 1000 bar more preferably from 580 to 750 bar. The application of HPLC allows for a fast separation (less than half an hour) with an increased sensitivity and a separation of more isomers than normal HPLC procedures. Moreover, inorganic salts are chromatographically better separated from the desired polar metabolites. Further advantages are a reduced tailing of the chromatographic peaks, especially for ketocarbonic acids or polyhydroxy acids and improved detection limits due to a better signal to noise ratio.

The separated polar metabolites are then analyzed in order to determine their chemical nature and/or in order to determine their structure. Such an analysis can be carried out by determining physical or chemical properties of the polar metabolites which subsequently can be compared to those properties of known molecules. Based on said comparison, a metabolite can be identified due to matching properties with known molecules. Moreover, the amount of a metabolite present in a sample can be determined quantitatively or semi-quantitatively by applying the method of the present invention.

Preferred techniques for analyzing the polar metabolites are mass spectrometry based or NMR-based techniques. Preferably, mass spectrometry is used, in particular, gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), highperformance liquid chromatography coupled mass spectrometry (HPLC-MS), quadrupole mass spectrometry, any sequentially coupled mass spectrometry, such as ESI-MS-MS or MS-MS-MS, inductively coupled plasma mass spectrometry (ICP-MS), pyrolysis mass spectrometry (Py-MS), ion mobility mass spectrometry or time of flight mass spectrometry (TOF). Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference. Most preferably, HPLC and ESI-MS/MS is used.

As an alternative or in addition to mass spectrometry techniques, the following techniques may be used for metabolite determination: nuclear magnetic resonance (NMR), magnetic resonance imaging (MRI), Fourier transform infrared analysis (FT-IR), ultra violet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado.

Moreover, the polar metabolites can also be analyzed by a specific chemical or biological assay. Said assay shall comprise means which allow to specifically detect a metabolite in the sample. Preferably, said means are capable of specifically recognizing the chemical structure of the metabolite or are capable of specifically identifying the metabolite based on its capability to react with other compounds or its capability to elicit a response in a biological read out system (e.g., induction of a reporter gene). Means which are capable of specifically recognizing the chemical structure of a metabolite are, preferably, antibodies or other proteins which specifically interact with chemical structures, such as receptors or enzymes. Specific antibodies, for instance, may be obtained using the metabolite as antigen by methods well known in the art. Antibodies as referred to herein include both polyclonal and monoclonal antibodies, as well as fragments thereof, such as Fv, Fab and F(ab)$_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the metabolite are, preferably, enzymes which are involved in the metabolic conversion of the said metabolite. Said enzymes may either use the metabolite as a substrate or may convert a substrate into the metabolite. Moreover, said antibodies may be used as a basis to generate oligopeptides which specifically recognize the metabolite. These oligopeptides shall, for example, comprise the enzyme's binding domains or pockets for the said metabolite. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the metabolite may also be identified based on its capability to react with other compounds, i.e. by a specific chemical reaction. Further, the metabolite may be analyzed due to its capability to elicit a response in a biological read out system. The biological response shall be detected as read out indicating the presence and/or the amount of the metabolite comprised by the sample. The biological response may be, e.g., the induction of gene expression or a phenotypic response of a cell or an organism.

The method of the present invention shall be, preferably, assisted by automation. For example, sample processing or pre-treatment during extraction and/or separation can be automated by robotics. Data processing and comparison is, preferably, assisted by suitable computer programs and databases. Automation as described herein before allows using the method of the present invention in high-throughput approaches.

Advantageously, it has been found in the studies underlying the present invention that the method of the present invention allows for an efficient extraction of polar metabolites from biological samples. In particular, carrying out the extraction at low temperatures prevents degradation of biological molecules due to a reduced overall chemical and/or biological reactivity, e.g., enzymes are kept inactive. The use of a phase separator as specified above in the extraction buffer results in a reduction of the freezing point of the aqueous phase, denaturation and efficient precipitation of proteins and a separation of hydrophobic enzymes and hydrophilic (polar) metabolites into different phases. Furthermore, it has been surprisingly found that the addition of a volatile neutral ammonium salt in high concentration increases the extraction rate significantly due to its ion-exchange properties. Moreover, the said volatile neutral ammonium salt can be removed from the extract at later stages and, thus, does not influence the analysis of the polar metabolites.

In a preferred embodiment of the method of the present invention the extract is treated by the following steps prior to step ii):
a) spin centrifugation of the aqueous phase,
b) lyophilization of the supernatant obtained in step a), and
c) dissolving the lyophilizate obtained in step b) in an analysis buffer comprising an ion pair generating agent.

In particular, if MS based analysis of the polar metabolites is envisaged as specified above, the aforementioned steps a) to c) are, preferably, carried out. The spin centrifugation of the aqueous phase efficiently removes cell debris from the remaining polar metabolites of the aqueous phase. Preferably, spin centrifugation is carried out by spin filtration using a membrane filter with a nominal cut off between 0.2 µm to 5 µm. The supernatant or filtrate of the spin centrifugation step comprising the polar metabolites and the polar components of the extraction buffer, such as the volatile neutral ammonium salt, will than be lyophilized by standard procedures. This process will also remove the volatile neutral ammonium salt by sublimation which, therefore, cannot influence the following steps of chromatographic separation or analysis of the polar metabolites. The resulting lyophilizate will be dissolved in an analysis buffer for chromatographic separation of the metabolites and analysis.

The analysis buffer used in accordance with the method of the present invention shall comprise an ion pair generating agent. Preferably, said agent is a tributylammonium cation, a triethylammonium cation, a tripropylammonium cation or an n-hexylammonium cation. These agents can be obtained as free amines which are than to be activated by a mass spectrometry-compatible acid, such as acetic acid or formic acid.

Preferably, the analysis buffer has a neutral to weakly acidic pH, more preferably, a pH of between 6.0 to 6.8, most preferably, 6.4 to 6.8.

In the following, particular aspects of preferred embodiments of the aforementioned method are described.

In a preferred embodiment of the method of the present invention, the biological sample is a cell suspension.

Prior to carrying out the method of the invention (i.e. prior to step i)), it is envisaged, preferably, to quench the biological sample, i.e. to immediately inhibit enzymatic activity and to inhibit chemical modifications due to, e.g., oxidation. However, it is desirable, in particular, in cases where intracellular metabolites are to be analyzed that the quenching procedure does not effect the metabolic composition by eliciting "bleeding" of the intracellular metabolites from inside the cells. In particular, for suspension cells, quenching procedures are crucial.

Therefore, the present invention also pertains to a method for quenching a biological sample comprising cellular material, the method comprising the steps of:
a) providing a centrifugation vial comprising a lower phase consisting of a pre-chilled quenching solution comprising a propane diol, or ethanediol, a hydrophobic intermediate phase consisting of an inert phase separator, and an upper phase consisting of the biological sample, wherein the lower phase has a higher density than the intermediate phase, and the intermediate phase has a higher density than the upper phase, and
b) centrifugation of the vial as to allow transferring the cellular material comprised by the biological sample from the upper phase to the lower phase.

Preferably, the propane diol is or comprises propane 1,2 diol. Also preferably, the inert phase separator is a hydrophobic fluid comprising a density $1.01 < \rho < 1.04$ (at 20° C.) and, more preferably, is or comprises a silicon oil.

As a result of the centrifugation, the suspension cells will be immediately transferred from the upper phase (e.g., a culture medium or buffer) into the lower phase where the pre-chilled quenching solution is present. The hydrophobic intermediate phase is immiscible with either of the upper or the lower phase and keeps both phases separate and minimizing diffusion processes and mixing of the upper and the lower phase.

Preferably, the lower phase has a temperature of −20 to −80° C. Particular preferred temperatures are, moreover, within the range of −25 to −80° C., −30° C. to −80° C., −35° C. to −80° C., −40° C. to −80° C., −45° C. to −80° C., −50° C. to −80° C., −55° C. to −80° C., −60° C. to −80° C., −65° C. to −80° C., −70° C. to −80° C. and, more preferably, the temperature is −70° C., −71° C., −71° C., −73° C., −74° C., −75° C., −76° C., −77° C., −78° C., −79° C., or −80° C.

Moreover, in a furthermore preferred embodiment of the aforementioned method, the upper aqueous phase is removed from the hydrophobic intermediate phase after centrifugation and an isotopically labeled standard is added to the lower phase. The said isotopically labeled standard will be used for recovery rate determination and comparison of individual experiments involving the method of the present invention. Preferably, the isotopically labeled standard is a cell extract of preferably microbial cells, more preferably from a yeast or bacterial culture, grown on a synthetic medium in the presence of an isotopically labeled substrate and/or an isotopically labeled ammonium salt. Preferably the substrate is labeled with $^{13}C$. Preferably, the isotopically labeled substrate is uniformly labeled $U^{13}C$-glucose or $U^{13}C$-glutamate, whereas the ammonium source is $^{15}N$ ammonium chloride or $^{15}N$ ammonium sulfate. The extract is particularly advantageous since various classes of biologically important molecules are represented therein but carry an isotopic signature which can be distinguished from the non-labeled form originating from the biological sample. Thus, the costly and cumbersome generation of a standard taking into account different classes of molecules can be efficiently circumvented at low costs. The added hydrophobic intermediate phase used to keep the aqueous phase and the quenching solution separate is removed according step i).

It is to be understood that, the aforementioned method for quenching can be, preferably, applied in the method for analyzing polar metabolites described above, in particular, in cases where suspension cells are to be investigated as biological samples. Thus, a cell suspension is subjected to quenching according to the aforementioned method prior to step i) of the method of the invention for analyzing polar metabolites.

In another preferred embodiment of the method of the invention, the biological sample is a culture of adherent cells grown on a membrane.

The term "membrane" as used herein refers to any solid support which can be transferred between different vials and which allows cells to adhere and grow thereon. Suitable membranes are well known in the art and include track edge membranes and any kind of hydrophilic or hydrophobic support suitable for the cultivation of adhering cells. More preferably, the membrane to be used in accordance with the method of the present invention is a track edge membrane. Advantageously, said membranes are destroyed during the extraction process and, therefore, release the adherent cells without the need of scrapping, tedious digestion, or other procedures which may interfere with efficient quenching.

Preferably, the culture of adherent cells grown on a membrane is subjected to quenching prior to step i) by immediately transferring the membrane to an extraction buffer as defined above having a temperature of between −20 to −80° C. Particular preferred temperatures for the extraction buffer are within the range of −25 to −80° C., −30° C. to −80° C., −35° C. to −80° C., −40° C. to −80° C., −45° C. to −80° C., −50° C. to −80° C., −55° C. to −80° C., −60° C. to −80° C., −65° C. to −80° C., −70° C. to −80° C. and, more preferably, the temperature is −70° C., −71° C., −71° C., −73° C., −74° C., −75° C., −76° C., −77° C., −78° C., −79° C., or −80° C.

Also preferably, the culture of adherent cells grown on a membrane is subjected to quenching prior to step i) by immediately transferring the membrane in liquid nitrogen. By said transfer a temperature of about −196° C. will be applied immediately. The transfer can be preferably achieved by transferring the membrane into a vessel and freezing the membrane in liquid nitrogen and, thus, applying the temperature of about −196° C. Alternatively, prior to step i) the membrane comprising the culture of adherent cells is rinsed with a washing puffer to clear the membrane from extracellular components derived from media. Subsequently, the membrane is quenched as described above.

In yet another preferred embodiment of the method of the present invention, said biological sample is a tissue sample. Preferably, said tissue is also subjected to quenching prior to step i) by immediate freezing of the tissue to a temperature of between −20 to −80° C. Particular preferred temperatures for quenching are within the range of −25 to −80° C., −30° C. to −80° C., −35° C. to −80° C., −40° C. to −80° C., −45° C. to −80° C., −50° C. to −80° C., −55° C. to −80° C., −60° C. to −80° C., −65° C. to −80° C., −70° C. to −80° C. and, more preferably, the temperature is −70° C., −71° C., −71° C., −73° C., −74° C., −75° C., −76° C., −77° C., −78° C., −79° C., or −80° C. Also preferably, said quenching prior to step i) can be achieved by immediate freezing of the tissue in liquid nitrogen, e.g., by applying a temperature of about −196° C.

All references referred to above are herewith incorporated by reference with respect to their entire disclosure content as well as their specific disclosure content explicitly referred to in the above description.

FIGURES

FIG. 1 shows a work flow of the method for analyzing polar metabolites from biological samples.

FIG. 2 reflects a twofold increase in the extraction yield for ADP and ATP, and a 5 to 12-fold increase in the extraction yield for coenzyme A and acetyl coenzyme A, respectively, and an up to threefold increase for nicotineaamide dinucleotides when the concentration of the used ammonium acetate buffer is increased from isotonic conditions to 1500 mM.

FIG. 3 shows a representative chromatogram of a tissue sample (human pankreas), freeze dried extract of 5 mg weighted sample (upper first chromatogram (3A) shows an overview XIC (XIC of-MRM (80 pairs): 87.0/43.0 amu expected RT:4.9 ID:PYR from Sample 21 (10 uL-C4) of liver 26 neu will (Turbo spray)), second chromatogram (3B) shows Redox and energy (XIC of-MRM (80 pairs): 305.8/143.0 amu expected RT:4.7 ID:GSH from Sample 21 (10 uL-C4) of liver 26 neu will (Turbo spray)), third chromatogram (3C) shows TCA (Krebs Cycle) (XIC of-MRM (80 pairs): 191.0/73.0 amu expected RT:9.7 ID:ISOCIT from Sample 21 (10 uL-C4) of liver 26 neu wiff (Turbo spray)), fourth chromatogram (3D) shows glycolysis (XIC of-MRM (80 pairs): 169.0/97.0 amu expected RT:6.6 ID:DHAP from Sample 21 (10 uL-C4) of liver 26 neu will (Turbo spray)). Intensity in cps are indicated on the y-axis, retention time in minutes (min) is indicated on the x-axis.

FIG. 4 shows the relative enrichment of U13C in extracts of polar metabolites based on the ratio found for intracellular U13C glucose/U12C-glucose; (A) conventional quenching method, (B) quenching by density centrifugation.

The invention will now be illustrated by the following Examples which are not intended to restrict or limit the scope of this invention.

EXAMPLES

Example 1

Quenching and Extraction a) Cell Supensions

350 μL of propane 1,2-diol were added to a number of extraction vials prefilled with five steel beads and cooled to −80° C. Thereafter, 350 μL of a silicon oil were added to each vial before storage at −80° C. until further use. A typical volume of one milliliter of an aqueous cell suspension was carefully added on top of the oil layer and the sample was immediately centrifuged at 15000*g for 2 min and 0° C. Following, the samples were immediately placed on dry ice and the upper phase was removed. Thereafter, an extraction buffer comprising an aqueous solution of 1.5 M ammonium acetate (4° C.), an isotopically labeled cell extract (4° C.), and dichloromethane (−80° C.) was added. Cell rupture, protein denaturing, and metabolite extraction was achieved in one step within 20 seconds via a bead milling process under cryogenic conditions (using a FastPrep24 device, MP Biomedicals Inc.). Phase separation was accomplished via centrifugation under the above mentioned conditions. In order to completely remove any cell debris, the upper polar phase was filtered over a 0.2 μm filter material via spin filtration using the conditions mentioned above. An aliquot of the filtrate was diluted with water, frozen at −80° C., and lyophilized subsequently.

b) Adherent Cell Cultures

A cultivation dish combined with a membrane-bottomed insert was used to cultivate adherent cell lines (e.g. tracked edge membranes, Nunc Inc.). For cell sampling, the membrane was excised and transferred to an extraction vial prefilled with five steel beads and a 2:1 mixture of dichloromethane and ethanol (−80° C.). For extraction, an aqueous solution of 1.5 M ammonium acetate (4° C.) and an isotopically labeled cell extract (4° C.) was added. Using the same bead milling procedure as described in a), cells and membrane were entirely disintegrated. Applying centrifugation conditions as described in a) removed proteins, cell debris and membrane residues and separated the sample into an upper, polar and a lower, apolar phase. The upper phase was collected and further processed as described under a).

c) Tissue Samples

For tissue sampling the tissue was immediately frozen at temperatures of liquid nitrogen and subsequently lyophilized. Following, 3-5 mg of dry tissue were overlaid with a 2:1 mixture of dichloromethane and ethanol (−80° C.). Finally, an aqueous solution of 1.5 M ammonium acetate (4° C.) and an isotopically labeled cell extract (4° C.) was added. The samples were further processed as described in b).

Example 2

Generation of Isotopically Labeled Cell Extracts

A yeast culture of Candida utilis (deposited under DSMZ sp. 2361) was grown in shake flasks on U13C-D-glucose (10 g/l) in YNB minimal medium without amino acids (Sigma). In order to maintain aerobic conditions the flasks were agitated at 180 rpm, at 28° C. using an orbital shaker. The cell harvest was performed by centrifguation of 200 ml yeast culture for 2 min at 1000*g and 4° C. (Falcon tube). Subsequently the cells were washed twice using a washing buffer consisting of 0.15 M ammonium acetate and 10 g/l U13C-D-glucose and consecutive centrifugation. The cell pellet was quenched using 7.5 mL of a 2:1 (v/v) dichloromethane/ethanol solution (−80° C.). Extraction was carried out under cryogenic conditions as described in a) by adding 2.5 ml of an aqueous solution of 1.5 M ammonium acetate to the quenched sample. Following the extraction the sample was centrifuged under conditions as described in a) and the upper phase comprising U13C-labeled metabolites was collected and stored at −80° C. until further use.

Example 3

Chromatographic Separation

For the chromatographic separation of phosphorylated and/or carboxylated polar metabolites ultra high pressure ion pairing liquid chromatography IP-HPLC was applied. A chromatographic gradient between a solvent A (deionized water) and a solvent B (50% acetonitrile, 50% water (v/v)) was processed, whereas a constant column flow of 0.4 mL/min and a column oven temperature of 45° C. was maintained. As a volatile additive tributylamine was added to both eluents and the pH value was adjusted to a pH value of 6.2 using glacial acetic acid to form the ion pairing tributylammonium cation. The lyophilized sample was dissolved in a low volume of eluent A before injection of 1 to 20 µL of the extract.

Example 4

Mass Spectrometry

Negative mode electrospray tandem mass spectrometry (-ESI-MSMS) was used to assess the polar metabolites separated by HPLC. The tandem MSMS was operated in the so-called scheduled or selected multiple reaction monitoring mode (sMRM) whereas unique mass adjustments with unit resolution were defined. Isotopically labeled and non-labeled forms of individual metabolites were distinguished by different mass traces.

Example 5

Increase of the Extraction Yield by a Volatile Extraction Buffer Applied in High Concentration Example 5 illustrates an increase in the extraction yield of several metabolites by using a volatile ammonium acetate buffer in high concentration for the extraction of cellular tissue. The added volatile buffer is removed during a subsequent lyophilization step, whereas the less volatile phosphorylated metabolites are retained. Thus, subjecting cellular tissue to highly saline buffers a number of protein associated metabolites are released to a much a higher extend than under conventional conditions. This finding is of particular importance for metabolites with low abundance in the sample. Beyond this, increasing the extraction yield of nicotineamides strongly affects the ratio between oxidized and reduced forms of NADPH, which is indicative for the availability of reducing equivalents in a cell or sample (FIG. 2).

Example 6

Representative Chromatogram

Example 6 shows a representative chromatogram for a freeze-dried tissue. 5 mg of dry sample were amended with an U13C-labeled yeast extract before extraction under cryogenic conditions. FIG. 3 shows a chromatogram of 70 mass traces (labeled/non-labeled) measured by negative mode ESI-MSMS using scheduled multiple reaction monitoring. Depending on the natural abundance in the sample or the labeled yeast the mass abundance ranges over three orders of magnitude. Besides an overview mode (XIC) three comprehensive mass extracts are depicted, which are indicative for the energy metabolism, the Krebs cycle (TCA), and the glycolysis, respectively.

Example 7

Improved Inhibition of Enzymatic Activity by Quenching Via Density Gradient Centrifugation A yeast culture of Candida utilis sp. 2361 was grown in YNB medium (Sigma) using 10 g L-1 non-labeled O-glucose and harvested at an optical density of 4.0 (600 nm, 1 cm light pass). In order to assess the bias caused by the quenching method the culture was (A) quickly passed over a 0.2 µm filter and washed (maximum 10 s) with a 150 mM ammonium acetate buffer containing 10 g L-1 of U13C-labeled D-glucose before quenching by cold solvents and (B) quenched immediately by using the density gradient centrifugation method, whereas the propane 1,2-diol phase was amended with an equivalent amount of U13C-D-glucose.

Using a standard quenching method (e.g. filtration and rapid cell wash) glycolytic intermediates, two Krebs cycle acids, and metabolites of the pentose phosphate pathway exhibited a significant 13C-enrichment. On the contrary, quenching the yeast cells by the new density gradient method, the absent enrichment of 13C in glycolytic and in other intermediates inherently proves the complete inactivation of glycolytic enzymes (FIG. 4).

The invention claimed is:

1. A method for analyzing polar metabolites comprising:
   i) extracting a biological sample with an extraction buffer comprising a phase separator and a volatile neutral ammonium salt under conditions which allow for immediate disruption of cells comprised by the biological sample,
   ii) spin centrifugation of an aqueous phase obtained from phase separation in step i),
   iii) lyophilization of a supernatant obtained from the spin centrifugation in step ii),
   iv) dissolving a lyophilizate of a supernatant obtained from the lyophilization in step iii) in an analysis buffer comprising an ion pair generating agent,
   v) separating polar metabolites comprised by the dissolved lyophilizate obtained in step iv) by chromatography, and
   vi) analyzing the separated polar metabolites obtained in step v).

2. The method of claim 1, wherein the phase separator comprises dichloromethane.

3. The method of claim 1, wherein the volatile ammonium salt is ammonium acetate, ammonium formiate, or ammonium hydrogen carbonate.

4. The method of claim 1, wherein the concentration of the volatile neutral ammonium salt is at least 0.5 M.

5. The method of claim 1, wherein the extracting a biological sample in step i) is carried out at an extraction temperature between -20 and -80° C.

6. The method of claim 1, wherein the ion pair generating agent is a tributylammonium cation, a triethylammonium cation, a tripropyl-ammonium cation, or an n-hexylammonium cation.

7. The method of claim 1, wherein the chromatography is UPLC or HPLC.

8. The method of claim 1, wherein the analyzing the separated polar metabolites obtained in step ii) comprises mass spectrometry.

9. The method of claim 8, wherein the mass spectrometry is ESI-MS/MS.

10. The method of claim 1, wherein the biological sample is a cell suspension.

11. The method of claim 1, wherein the biological sample is a culture of adherent cells grown on a membrane.

12. The method of claim 11, wherein the culture of adherent cells grown on a membrane is subjected to quenching prior to step i) by transferring the membrane to extraction buffer comprising a phase separator and a volatile neutral ammonium salt having a temperature between −20 and −80° C.

13. The method of claim 11, wherein the culture of adherent cells grown on a membrane is subjected to quenching prior to step i) by transferring the membrane to liquid nitrogen.

14. The method of claim 1, wherein the biological sample is a tissue sample.

15. The method of claim 14, wherein the tissue is subjected to quenching prior to step i) by immediate freezing of the tissue to a temperature between −20 and −80° C. or by applying liquid nitrogen.

\* \* \* \* \*